US010117031B2

(12) United States Patent
Hartley et al.

(10) Patent No.: US 10,117,031 B2
(45) Date of Patent: *Oct. 30, 2018

(54) SOUND PROCESSOR APPARATUS WITH DUAL-MODE EARHOOK INTERFACE ASSEMBLY

(71) Applicant: Advanced Bionics AG, Staefa (CH)

(72) Inventors: Lee F. Hartley, Carlsbad, CA (US); Lakshmi N. Mishra, Carlsbad, CA (US); R. Tissa Karunasiri, Valencia, CA (US); Logan P. Palmer, Santa Monica, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/435,288

(22) Filed: Feb. 16, 2017

(65) Prior Publication Data
US 2017/0223470 A1 Aug. 3, 2017

Related U.S. Application Data

(63) Continuation of application No. 14/761,003, filed as application No. PCT/US2013/021606 on Jan. 15, 2013, now Pat. No. 9,615,180.

(51) Int. Cl.
H04R 25/00 (2006.01)
H04R 1/10 (2006.01)
(Continued)

(52) U.S. Cl.
CPC ....... *H04R 25/556* (2013.01); *A61N 1/36036* (2017.08); *H04R 1/105* (2013.01);
(Continued)

(58) Field of Classification Search
CPC .... H04R 25/43; H04R 25/556; H04R 25/604; H04R 25/606; H04R 25/608;
(Continued)

(56) References Cited

U.S. PATENT DOCUMENTS

2002/0138115 A1 9/2002 Baumann et al.
2004/0044389 A1 3/2004 Crawford
(Continued)

FOREIGN PATENT DOCUMENTS

CN 201105090 Y 8/2014

OTHER PUBLICATIONS

International Search Report and Written Opinion received in International Application No. PCT/US13/021606, dated Jul. 31, 2013.
(Continued)

*Primary Examiner* — Joshua Kaufman
(74) *Attorney, Agent, or Firm* — ALG Intellectual Property, LLC

(57) ABSTRACT

An exemplary sound processor apparatus includes 1) an earhook interface assembly that includes a plurality of contacts and that is configured to interchangeably connect to a microphone assembly and an EAS receiver assembly by way of the plurality of contacts, and 2) a control module communicatively coupled to the plurality of contacts. In some examples, the control module uses the plurality of contacts as output ports to output one or more EAS signals to the EAS receiver assembly while the EAS receiver assembly is connected to the earhook interface assembly.

20 Claims, 8 Drawing Sheets

(51) Int. Cl.
*H04R 25/02* (2006.01)
*A61N 1/36* (2006.01)

(52) U.S. Cl.
CPC ........... *H04R 25/02* (2013.01); *H04R 25/554* (2013.01); *H04R 25/65* (2013.01); *H04R 2225/021* (2013.01); *H04R 2225/59* (2013.01); *H04R 2225/61* (2013.01); *H04R 2225/63* (2013.01); *H04R 2225/67* (2013.01)

(58) Field of Classification Search
CPC .......... H04R 2225/021; H04R 2225/61; H04R 2225/63; H04R 2225/67; A61N 1/36032; A61N 1/0541
See application file for complete search history.

(56) References Cited

U.S. PATENT DOCUMENTS

| | | | |
|---|---|---|---|
| 2005/0261748 A1* | 11/2005 | van Dijk | A61N 1/36036 607/57 |
| 2006/0074341 A1 | 4/2006 | Causevic et al. | |
| 2011/0116669 A1 | 5/2011 | Karunasiri | |
| 2012/0109297 A1 | 5/2012 | Van den Heuvel | |

OTHER PUBLICATIONS

First Office Action received in Chinese Patent Application No. 201380070418.3, dated Jul. 5, 2016.
Non-Final Office Action received in U.S. Appl. No. 14/761,003 dated Sep. 22, 2016.

\* cited by examiner

SOUND PROCESSOR APPARATUS WITH DUAL-MODE EARHOOK INTERFACE ASSEMBLY

RELATED APPLICATIONS

The present application is a continuation application of U.S. patent application Ser. No. 14/761,003, filed Jul. 14, 2015, which application is a U.S. National Stage Entry of PCT Application No. PCT/US13/21606, filed Jan. 15, 2013. The contents of these applications are incorporated herein by reference in their respective entireties.

BACKGROUND INFORMATION

Various types of auditory prosthesis systems have been developed to assist patients who have severe (e.g., complete) hearing loss. For example, cochlear implant systems may provide a sense of hearing for sensorineural hearing loss patients by providing electrical stimulation representative of sound directly to stimulation sites within the cochlea. As another example, electro-acoustic stimulation ("EAS") systems may assist patients with some degree of residual hearing in the low frequencies (e.g., below 1000 Hz) by providing acoustic stimulation representative of low frequency audio content and electrical stimulation representative of high frequency content.

Many auditory prosthesis systems include a sound processor apparatus (e.g., a behind-the-ear ("BTE") sound processing unit) configured to be located external to the patient. The sound processor apparatus may perform a variety of functions, such as processing audio signals presented to the patient, controlling an operation one or more implantable devices (e.g., one or more cochlear implants), and providing power to the one or more implantable devices.

Some conventional BTE sound processor apparatuses include an earhook interface assembly that facilitates selective coupling of a microphone assembly (e.g., a "T-mic") to the BTE sound processor apparatuses. The microphone assembly may include a microphone configured to be located within the concha of the ear near the entrance to the ear canal and may be configured to detect audio signals presented to the patient. The microphone assembly may also provide structural support for the patient to wear the sound processor on the ear. When the patient prefers to use another audio input source (e.g., another microphone included in the auditory prosthesis system or an auxiliary audio input source), the patient may connect a standard earhook to the earhook interface assembly in place of the microphone assembly. In this manner, the patient may still wear the sound processor apparatus on the ear.

It may be desirable to utilize the earhook interface assembly for other types of accessories. Unfortunately, this is not possible with conventional earhook interface assemblies.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
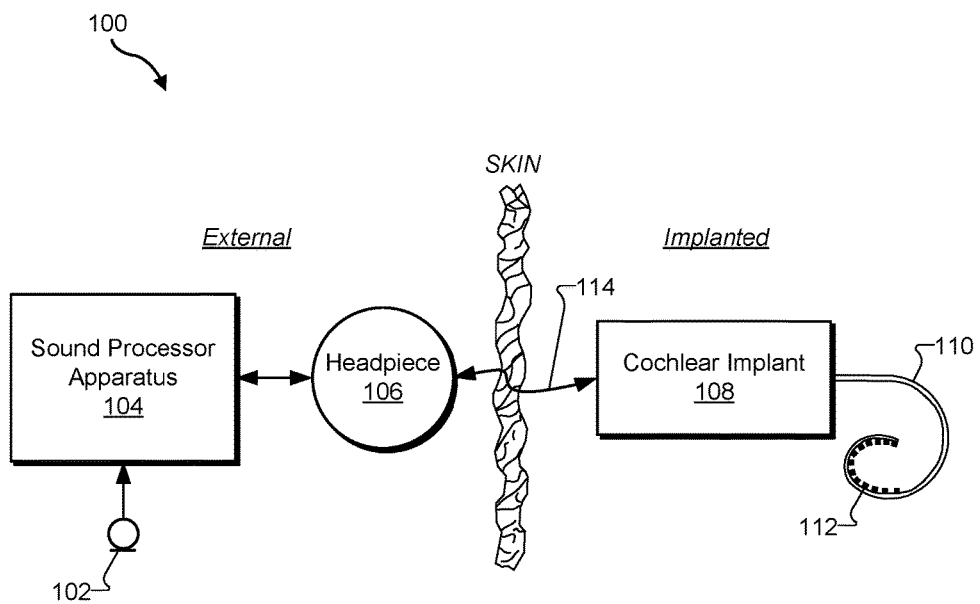
FIG. 1 illustrates an exemplary auditory prosthesis system according to principles described herein.

A sound processor apparatus with a dual-mode earhook interface assembly is described herein. As will be described below, an exemplary sound processor apparatus included in an auditory prosthesis system may include an earhook interface assembly that includes a plurality of contacts (e.g., pins) and that is configured to interchangeably connect to a microphone assembly (i.e., a device that detects audio signals presented to a patient fitted with the auditory prosthesis system) and an electro-acoustic stimulation ("EAS") receiver assembly (i.e., a device configured to provide acoustic stimulation to the patient) by way of the plurality of contacts. The sound processor apparatus may further include a control module communicatively coupled to the plurality of contacts and that is configured to selectively operate in an input mode or in an output mode. While operating in the input mode, the control module uses the plurality of contacts as input ports to receive one or more audio signals detected by the microphone assembly while the microphone assembly is connected to the earhook interface assembly. While operating in the output mode, the control module uses the plurality of contacts as output ports to output one or more EAS signals to the EAS receiver assembly while the EAS receiver assembly is connected to the earhook interface assembly.

To illustrate, the control module may be configured to selectively operate in accordance with a plurality of different programs. Each program may be associated with either the microphone assembly or the EAS receiver assembly. A user (e.g., a patient fitted with the auditory prosthesis system) may select a particular program in order to use a desired accessory that connects to the earhook interface assembly (i.e., either the microphone assembly or the EAS receiver assembly).

For example, the user may desire to initially utilize the microphone assembly. To that end, the user may connect the microphone assembly to the earhook interface assembly and instruct the control module (e.g., by providing one or more user input commands) to operate in accordance with a particular program that utilizes the microphone assembly. In response, the control module may begin operating in accordance with the selected program by using the plurality of contacts as input ports to receive one or more audio signals detected by the microphone assembly while the microphone assembly is connected to the earhook interface assembly.

The user may subsequently desire to utilize the EAS receiver assembly in place of the microphone assembly. To that end, the user may disconnect the microphone assembly from the earhook interface assembly, connect the EAS receiver assembly to the earhook interface assembly in place of the microphone assembly, and instruct the control module to operate in accordance with a different program that utilizes the EAS receiver assembly. In response, the control module may begin operating in accordance with the different program by using the plurality of contacts as output ports to output one or more EAS signals to the EAS receiver assembly while the EAS receiver assembly is connected to the earhook interface assembly.

By overloading the contacts included in the earhook interface assembly in this manner (i.e., by using the same contacts to perform different operations with respect to different external components coupled to the earhook interface assembly), various benefits may be realized. For example, the number of contacts required for the control module to interact with a microphone assembly and an EAS receiver assembly by way of the same earhook interface assembly may be reduced compared to earhook interface assemblies included in conventional sound processor apparatuses. This, in turn, may facilitate a lighter, less bulky, and more aesthetically pleasing sound processor apparatus. Furthermore, the sound processor apparatus described herein may allow a user to switch between using a microphone assembly and an EAS receiver assembly on the fly simply by swapping in the desired external component (i.e., connecting the desired component to the earhook interface assembly).

FIG. 1 illustrates an exemplary auditory prosthesis system 100. Auditory prosthesis system 100 may include a microphone 102, a sound processor apparatus 104, a headpiece 106 having a coil disposed therein, a cochlear implant 108, and a lead 110 with a plurality of electrodes 112 disposed thereon. Additional or alternative components may be included within auditory prosthesis system 100 as may serve a particular implementation.

As shown, auditory prosthesis system 100 may include various components configured to be located external to a patient including, but not limited to, a microphone 102, a sound processor apparatus 104, and a headpiece 106. Auditory prosthesis system 100 may further include various components configured to be implanted within the patient including, but not limited to, a cochlear implant 108 and a lead 110 with a plurality of electrodes 112 disposed thereon. As will be described in more detail below, additional or alternative components may be included within auditory prosthesis system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may be implemented by a "T-Mic" or the like that is configured to be placed within the concha of the ear near the entrance to the ear canal. Such a microphone may be included in a microphone assembly, as will be described in more detail below. Additionally or alternatively, microphone 102 may be implemented by one or more microphones disposed within headpiece 106, one or more microphones disposed within sound processor apparatus 104, and/or any other suitable microphone as may serve a particular implementation.

Sound processor apparatus 104 (i.e., one or more components included within sound processor apparatus 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor apparatus 104 may process the one or more audio signals in accordance with a selected sound processing strategy or program to generate appropriate stimulation parameters for controlling cochlear implant 108. Sound processor apparatus 104 may include or be implemented by a behind-the-ear ("BTE") unit, a body worn device, and/or any other sound processing unit as may serve a particular implementation.

In some examples, sound processor apparatus 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor apparatus 104 and may include an external antenna (e.g., a coil and/or one or more wireless communication components) configured to facilitate selective wireless coupling of sound processor apparatus 104 to cochlear implant 108. Headpiece 106 may be additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor apparatus 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor apparatus 104

(e.g., an audio signal detected by microphone 102) in accordance with one or more stimulation parameters transmitted thereto by sound processor apparatus 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
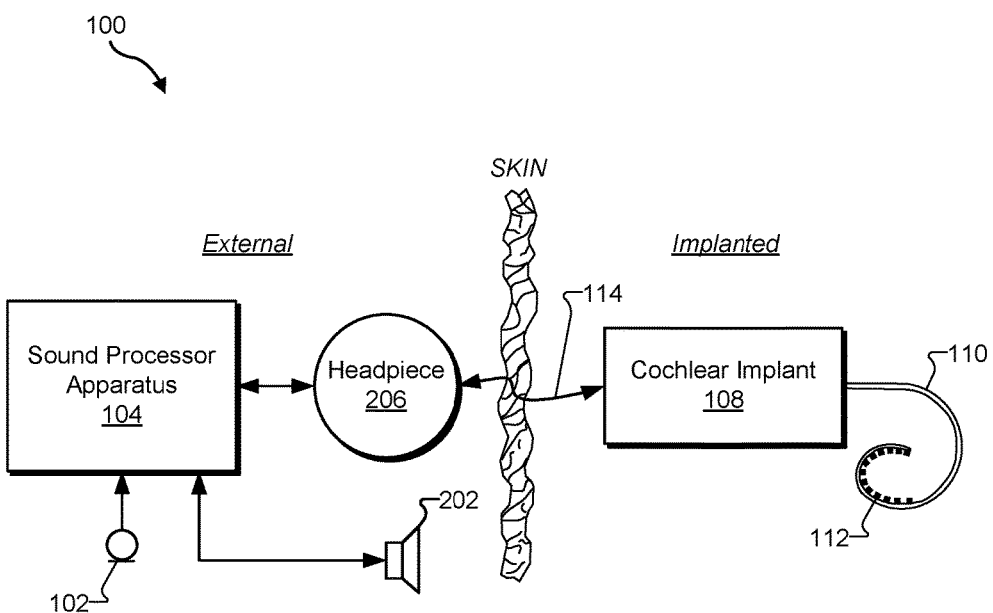
FIG. 2 illustrates an implementation of the auditory prosthesis system of FIG. 1 according to principles described herein.

The auditory prosthesis system 100 illustrated in FIG. 1 may be referred to as a cochlear implant system because sound processor apparatus 104 is configured to direct cochlear implant 108 to generate and apply electrical stimulation representative of audio content (e.g., one or more audio signals) to one or more stimulation sites within the patient by way of one or more of electrodes 112. FIG. 2 illustrates another implementation of auditory prosthesis system 100 in which auditory prosthesis system 100 is further configured to provide acoustic stimulation to the patient. Hence, the implementation shown in FIG. 2 may be referred to as an electro-acoustic stimulation ("EAS") system.

As shown, auditory prosthesis system 100 may further include a receiver 202 (also referred to as a loudspeaker). In this configuration, sound processor apparatus 104 may be configured to direct receiver 202 to apply acoustic stimulation representative of audio content included in a relatively low frequency band (e.g., below 1000 Hz) to the patient and cochlear implant 108 to apply electrical stimulation representative of audio content included in a relatively high frequency band (e.g., above 1000 Hz) to one or more stimulation sites within the patient by way of one or more of electrodes 112. Sound processor apparatus 104 may also be configured to deliver broadband audio content to both the receiver 202 and the cochlear implant 108 or to provide a certain degree of frequency overlap between the two.

Figure 3:
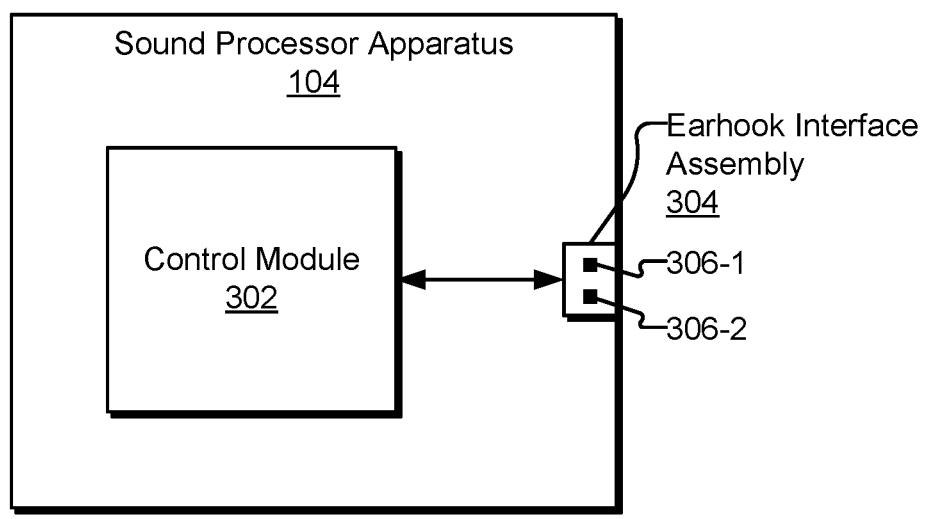
FIG. 3 illustrates exemplary components that may be included within a sound processor apparatus according to principles described herein.

FIG. 3 illustrates exemplary components that may be included within sound processor apparatus 104. As shown, sound processor apparatus 104 may include a control module 302 and an earhook interface assembly 304 that includes a plurality of contacts 306 (e.g., contacts 306-1 and 306-2). It will be recognized that sound processor apparatus 104 may include additional or alternative components as may serve a particular implementation. In some examples, one or more of the components included in sound processor apparatus 104 (e.g., control module 302 and earhook interface assembly 304) may be housed within a single casing.

Control module 302 may be configured to perform one or more operations with respect to one or more components connected to or otherwise communicative coupled to sound processor apparatus 104. For example, control module 302 may be configured to control an operation of cochlear implant 108, receiver 202, and/or any other device associated with providing electrical and/or acoustic stimulation to a patient. To illustrate, control module 302 may process an audio signal presented to the patient, generate one or more stimulation parameters based on the processing of the audio signal, and direct cochlear implant 108 to generate and apply electrical stimulation representative of the audio signal to the patient in accordance with the stimulation parameters (e.g., by transmitting the stimulation parameters to cochlear implant 108).

Control module 302 may be additionally or alternatively configured to interact with one or more external components connected to sound processor apparatus 104 by way of earhook interface assembly 304. To this end, control module may overload contacts 306 with a plurality of functions. Exemplary manners in which this may be performed will be described below.

Control module 302 may be implemented by any suitable combination of integrated circuits, circuitry, processors, and/or computing devices configured to perform one or more of the operations and/or functions described herein. Exemplary implementations of control module 302 will be described below.

Earhook interface assembly 304 may be configured to interchangeably connect to a plurality of external components. For example, earhook interface assembly 304 may interchangeably connect to a microphone assembly, an EAS receiver assembly, an earhook assembly, and/or any other component as may serve a particular implementation.

To facilitate this interchangeable connectivity, earhook interface assembly 304 may include a plurality of contacts 306. The number of contacts 306 may vary as may serve a particular implementation. For example, as shown in FIG. 3, earhook interface assembly 304 may include two contacts (i.e., first and second contacts 306-1 and 306-2). In some examples, earhook interface assembly 304 includes only two contacts. In other examples, earhook interface assembly 304 may include more than two contacts (e.g., in configurations where it is desirable for earhook interface assembly 304 to connect to components other than those listed above). For purposes of the examples described herein, it will be assumed that earhook interface assembly 304 includes only two contacts (i.e., contacts 306-1 and 306-2).

Each contact 306 may include any type of conductive contact (e.g., a male contact such as a pin or a female contact such as a receptacle) as may serve a particular implementation. Each contact 306 may be configured to be electrically coupled to a corresponding contact included in an interface assembly associated with (e.g., integrated into and/or otherwise coupled to) an external component while the external component is connected to earhook interface assembly 304.

Earhook interface assembly 304 may be referred to as "dual mode" because it facilitates control module 302 being able to selectively operate in either an "input mode" or an "output mode." While operating in the input mode, control module 302 uses contacts 306 as input ports to receive one or more audio signals detected by a microphone assembly while the microphone assembly is connected to earhook interface assembly 304. While operating in the output mode, control module 302 uses contacts 306 as output ports to output one or more EAS signals to an EAS receiver assembly while the EAS receiver assembly is connected to earhook interface assembly 304. This will be described in more detail below.

Figure 4:
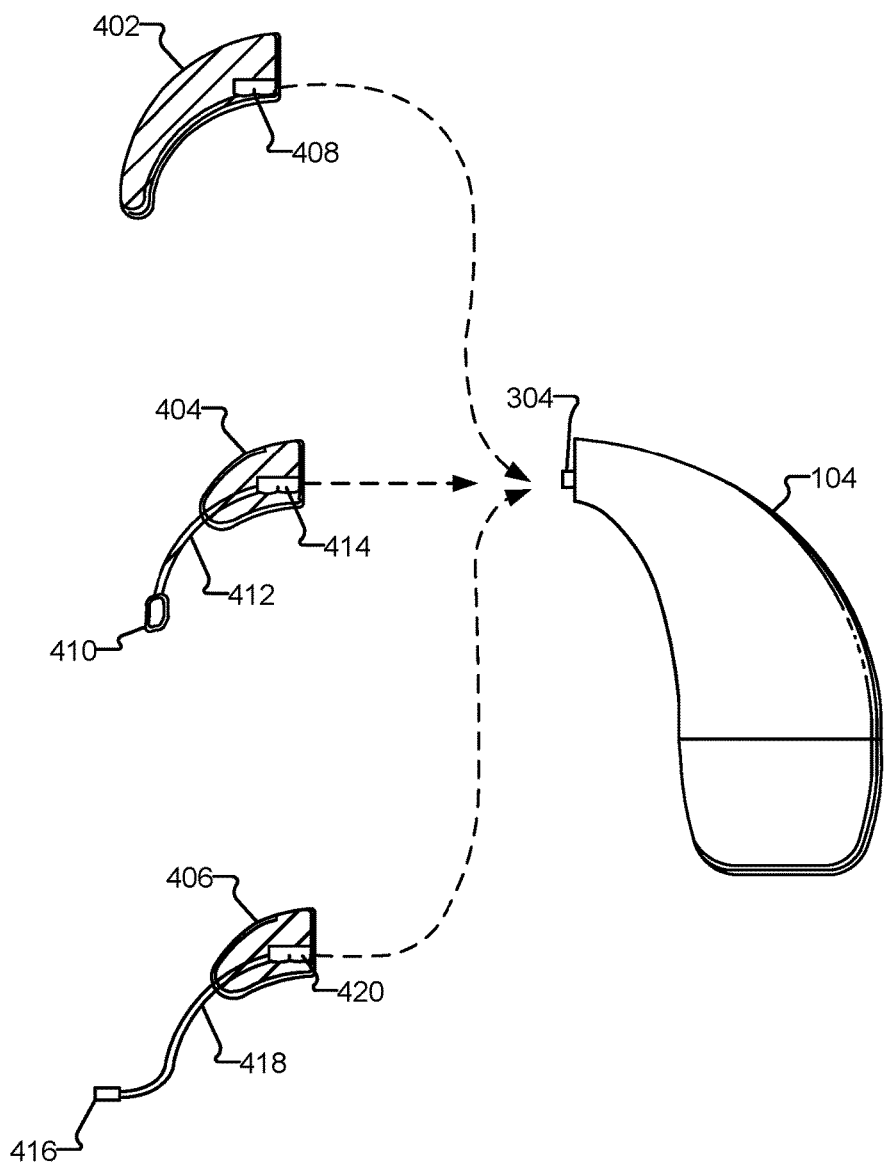
FIG. 4 shows that an earhook assembly, a microphone assembly, and an EAS receiver assembly may be interchangeably connected to an earhook interface assembly of a sound processor apparatus according to principles described herein.

FIG. 4 shows that an earhook assembly 402, a microphone assembly 404, and an EAS receiver assembly 406 may be interchangeably connected to earhook interface assembly 304 of sound processor apparatus 104 (which, as shown, may be implemented by a BTE assembly).

Earhook assembly 402 may not have any other functionality other than to provide structural support for the patient to wear sound processor apparatus 304 on the ear. A user may connect earhook assembly 402 to earhook interface assembly 304 in any suitable manner. For example, the user may attach a connector 408 that includes two contacts corresponding to contacts 306 of earhook interface assembly 304.

Microphone assembly 404 (e.g., a T-mic assembly) may be configured to detect audio signals presented to the patient.

To this end, microphone assembly may include a microphone 410 mounted near the tip of a boom 412 that extends from a connector 414. Connector 414 may include two contacts corresponding to contacts 306 of earhook interface assembly 304 and may be used to mechanically attach microphone assembly 404 to earhook interface assembly 304. As will be described below, connector 414 may also be used to electrically connect two signal lines included within microphone assembly 404 (e.g., a signal line used to transmit signals representative of audio signals detected by microphone 410 and a signal line used as ground) with corresponding circuitry included in sound processor assembly 104.

EAS receiver assembly 406 may be configured to provide acoustic stimulation to the patient. To this end, EAS receiver assembly 406 may include a receiver 416 disposed at a distal portion of a cable 418 that is attached to a connector 420. Connector 420 may include two contacts corresponding to contacts 306 of earhook interface assembly 304 and may be used to mechanically attach EAS receiver assembly 406 to earhook interface assembly 304. As will be described below, connector 420 may also be used to electrically connect two signal lines included within EAS receiver assembly 406 (e.g., two wires included within cable 418 that are electrically coupled to receiver 416) with corresponding circuitry included in sound processor assembly 104.

Figure 5:
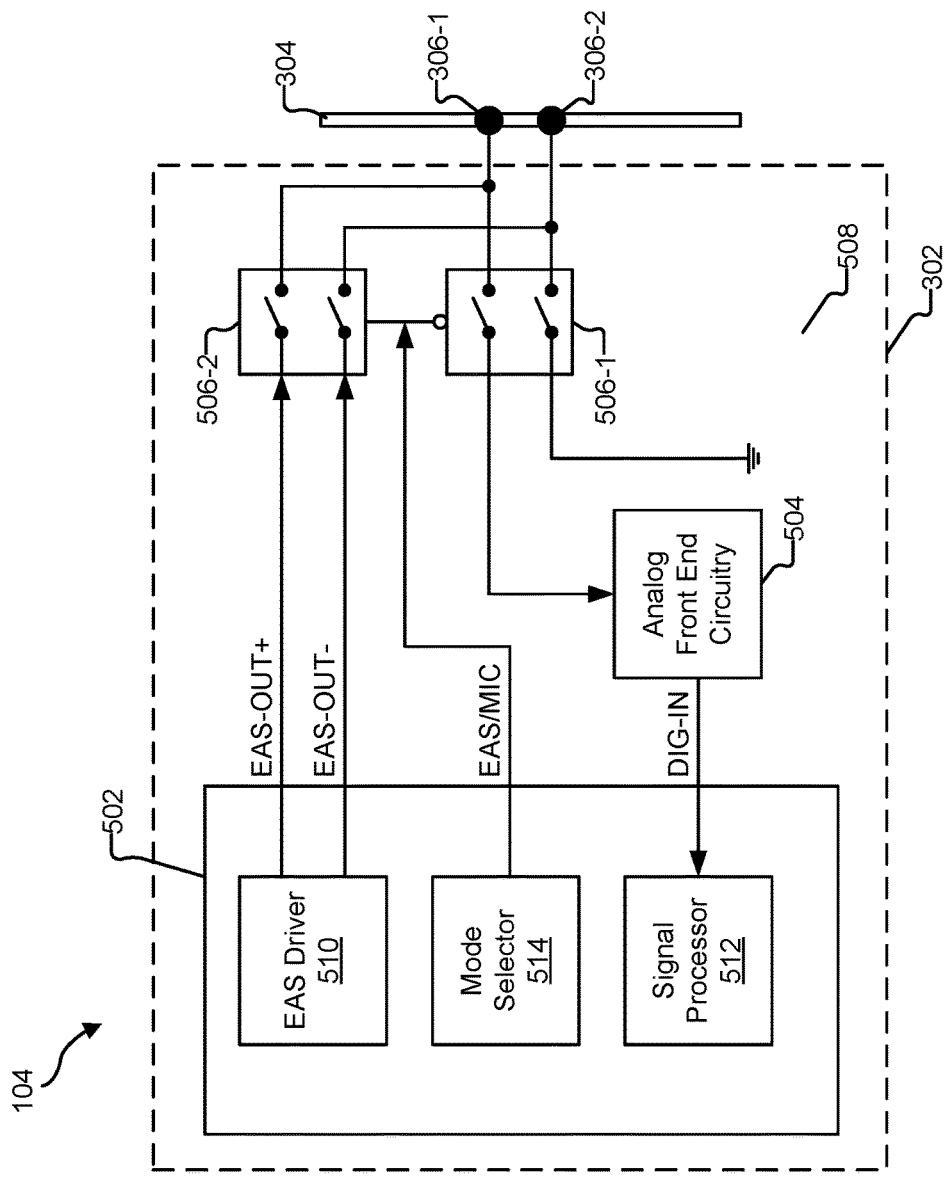
FIG. 5 shows an exemplary configuration of a sound processor apparatus according to principles described herein.

Control module 302 and earhook interface assembly 304 may be implemented in any suitable manner. For example, FIG. 5 shows an exemplary configuration of sound processor apparatus 104 wherein control module 302 is implemented by an integrated circuit ("IC") 502 and various on-board electrical components (e.g., analog front end circuitry 504 and switches 506-1 and 506-2) disposed on a printed circuit board 508.

IC 502 may be implemented by any suitable combination of integrated circuits as may serve a particular implementation. As shown, IC 502 may include various components configured to perform various functions associated with either a microphone assembly (e.g., microphone assembly 404) or a EAS receiver assembly (e.g., EAS receiver assembly 406) connected to earhook interface assembly 304 by way of contacts 306-1 and 306-2.

For example, IC 502 may include an EAS driver 510 configured to output EAS signals (e.g., one or more signals configured to direct the EAS receiver assembly to apply acoustic stimulation to the patient) by way of data lines labeled EAS-OUT+ and EAS-OUT− to an EAS receiver assembly while the EAS receiver assembly is connected to earhook interface assembly 304. IC 502 may also include a signal processor 512 configured to process signals provided by analog front end circuitry 504 (e.g., digital signals representative of audio signals detected by a microphone assembly while the microphone assembly is connected to earhook interface assembly 304). As shown, analog front end circuitry 504 may provide these signals by way of a data line labeled DIG-IN. IC 502 may also include a mode selector 514 configured to control an operation of switches 506 depending on a particular mode in which control module 302 is to operate. As will be described below, this may be performed by asserting or deasserting a control line labeled EAS/MIC.

Analog front end circuitry 504 may be configured to process audio signals detected by a microphone assembly while the microphone assembly is connected to earhook interface assembly 304. For example, analog front end circuitry 504 may include an analog-to-digital converter configured to convert analog audio signals into digital signals and/or any other suitable front end circuitry.

Switches 506 may be configured to facilitate selectively connect contacts 306-1 and 306-2 to EAS driver 510 or to analog front end circuitry 504 and ground. This may allow control module 302 to selectively operate in an input mode or an output mode.

For example, to operate in an input mode, control module 302 may close switch 506-1 and open switch 506-2. This may be performed, for example, by mode selector 514 deasserting the EAS/MIC control signal. In some alternative examples, the logic controls for switches 506-1 and 506-2 may be separated in order to reduce signal coupling.

Figure 6:
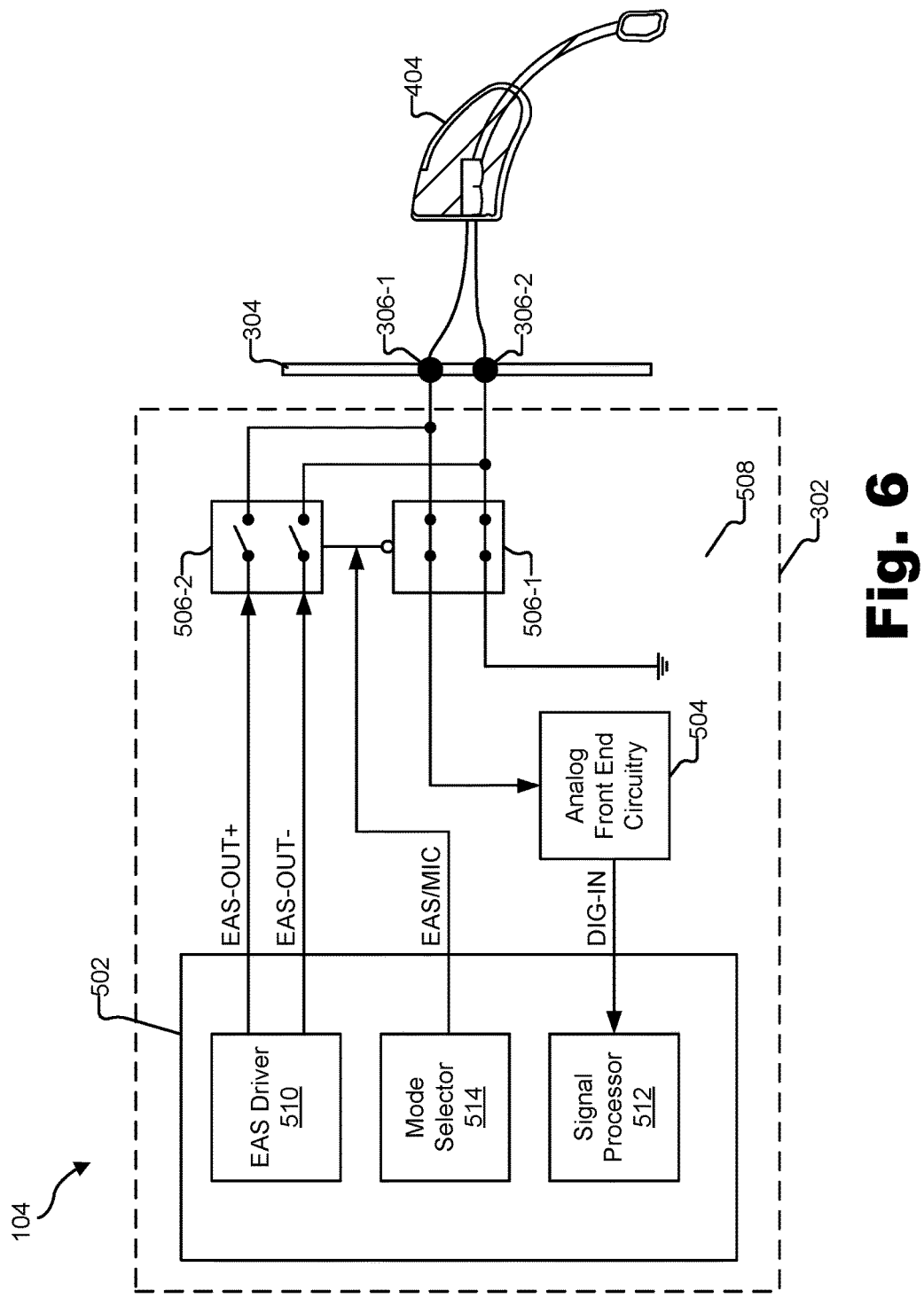
FIG. 6 shows an exemplary configuration in which a microphone assembly is connected to an earhook interface assembly of a sound processor apparatus according to principles described herein.

FIG. 6 shows an exemplary configuration in which microphone assembly 404 is connected to earhook interface assembly 304 by way of contacts 306-1 and 306-2. As shown, the EAS/MIC control signal has been deasserted in order to close switch 506-1 and open switch 506-2. This causes contact 306-1 to be electrically connected to analog front end circuitry 504 and contact 306-2 to ground, thereby facilitating interaction by control module 302 with microphone assembly 404.

Figure 7:
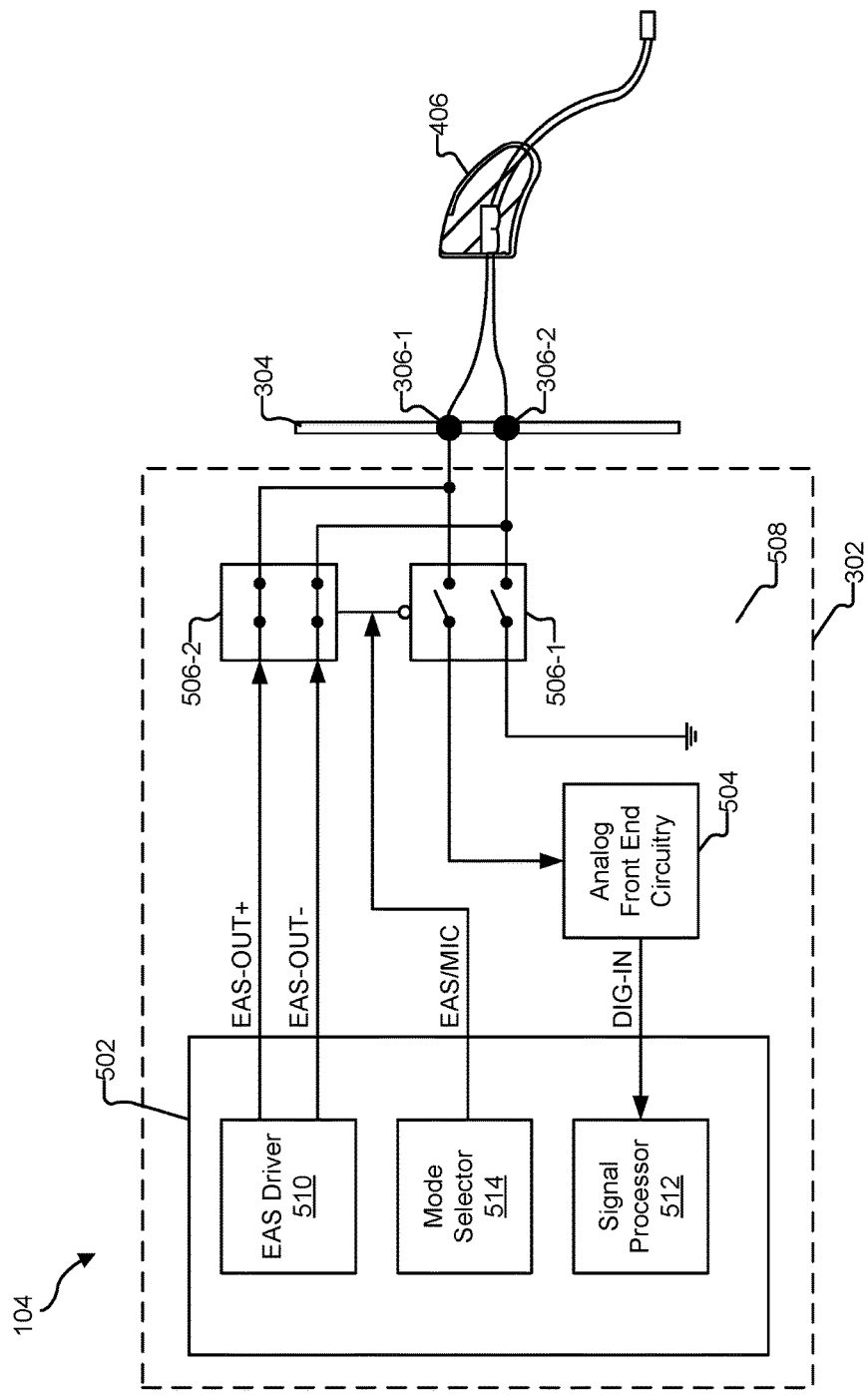
FIG. 7 shows an exemplary configuration in which an EAS receiver assembly is connected to an earhook interface assembly of a sound processor apparatus according to principles described herein.

To operate in an output mode, control module 302 may open switch 506-1 and close switch 506-2. To illustrate, a user may disconnect microphone assembly 404 from earhook interface assembly 304 and connect EAS receiver assembly 406 to earhook interface assembly 304. This configuration is shown in FIG. 7. As shown in FIG. 7, the EAS/MIC control signal has been asserted in order to open switch 506-1 and close switch 506-2. This causes contacts 306-1 and 306-2 to be electrically connected to EAS driver 510, thereby facilitating interaction by control module 302 with EAS receiver assembly 406. For example, EAS driver 510 may output one or more EAS signals to EAS receiver assembly 406 in accordance with a differential signaling heuristic. Differential signaling provides more noise immunity than single-ended signaling, which is used in conventional sound processor apparatuses. Differential signaling may also reduce EMI emissions compared to single-ended signaling.

In some examples, switches 506 (and other circuitry included in control module 302) may be configured to isolate input lines (e.g., the lines connecting switch 506-1 to analog front end circuitry 504 and ground) from output lines (e.g., the lines labeled EAS-OUT+ and EAS-OUT−. In this manner, the input and output lines may not interfere with each other.

Control module 302 may switch between operating in the input mode and the output mode in any suitable manner. For example, control module 302 may maintain data representative of different programs (e.g., operating programs). Each program may be configured to utilize either microphone assembly 404 or EAS receiver assembly 406. In this manner, when a user (e.g., the patient) instructs control module 302 to operate in accordance with a particular program, control module 302 may assert or deassert the EAS/MIC control signal accordingly.

For example, control module 302 may maintain data representative of a first program that utilizes microphone assembly 404 and a second program that utilizes the EAS receiver assembly 406. A user may connect microphone assembly 404 to earhook interface assembly 304 and provide a command (e.g., by interacting with a program selection switch or in any other suitable manner) for control module 302 to initially operate in accordance with the first program. In response, control module 302 may deassert the EAS/MIC control signal in order to close switch 506-1 and open switch 506-2. In this manner, control module 302 may use contacts 306-1 and 306-2 as input ports to receive one or more audio signals detected by microphone assembly 404 while microphone assembly 404 is connected to earhook interface assembly 304.

The user may subsequently connect EAS receiver assembly 406 to earhook interface assembly 304 in place of microphone assembly 404 and provide a command for control module 302 to switch from operating in accordance with the first program to operating in accordance with the second program. In response, control module 302 may assert the EAS/MIC control signal in order to open switch 506-1 and close switch 506-2. In this manner, control module 302 may use contacts 306-1 and 306-2 as output ports to output one or more EAS signals to EAS receiver assembly 406 while EAS receiver assembly 406 is connected to earhook interface assembly 304.

Additionally or alternatively, control module 302 may automatically switch between operating in the input mode and the output mode by detecting which external component (i.e., microphone assembly 404 or EAS receiver assembly 406) is connected to earhook interface assembly 304.

For example, control module 302 may detect a connection of microphone assembly 404 to earhook interface assembly 304. This may be performed in any suitable manner. For example, control module 302 may detect an impedance of microphone assembly 404 while microphone assembly 404 is connected to earhook interface assembly 304 and determine that the impedance corresponds to microphone assembly 404 (as opposed to EAS receiver assembly 406). Control module 302 may detect the connection of microphone assembly 404 to earhook interface assembly 304 in any other suitable manner.

In response to detecting the connection of microphone assembly 404 to earhook interface assembly 304, control module 302 may automatically switch to operating in the input mode (e.g., by deasserting the EAS/MIC control signal). In this configuration, control module 302 may use contacts 306-1 and 306-2 as input ports to receive one or more audio signals detected by microphone assembly 404 while microphone assembly 404 is connected to earhook interface assembly 304.

As another example, control module 302 may detect a connection of EAS receiver assembly 406 to earhook interface assembly 304. This may be performed in any suitable manner. For example, control module 302 may detect an impedance of EAS receiver assembly 406 while EAS receiver assembly 406 is connected to earhook interface assembly 304 and determine that the impedance corresponds to EAS receiver assembly 406 (as opposed to microphone assembly 404). Control module 302 may detect the connection of EAS receiver assembly 406 to earhook interface assembly 304 in any other suitable manner.

In response to detecting the connection of EAS receiver assembly 406 to earhook interface assembly 304, control module 302 may automatically switch to operating in the output mode (e.g., by asserting the EAS/MIC control signal). In this configuration, control module 302 may use contacts 306-1 and 306-2 as output ports to output one or more EAS signals to EAS receiver assembly 406 while EAS receiver assembly 406 is connected to earhook interface assembly 304.

In some examples, control module 302 may be configured to use an audio source other than microphone assembly 404 while microphone assembly 404 is disconnected from earhook interface assembly 304. For example, control module 302 may use another microphone included in auditory prosthesis system 100, an auxiliary audio source, etc.

Figure 8:
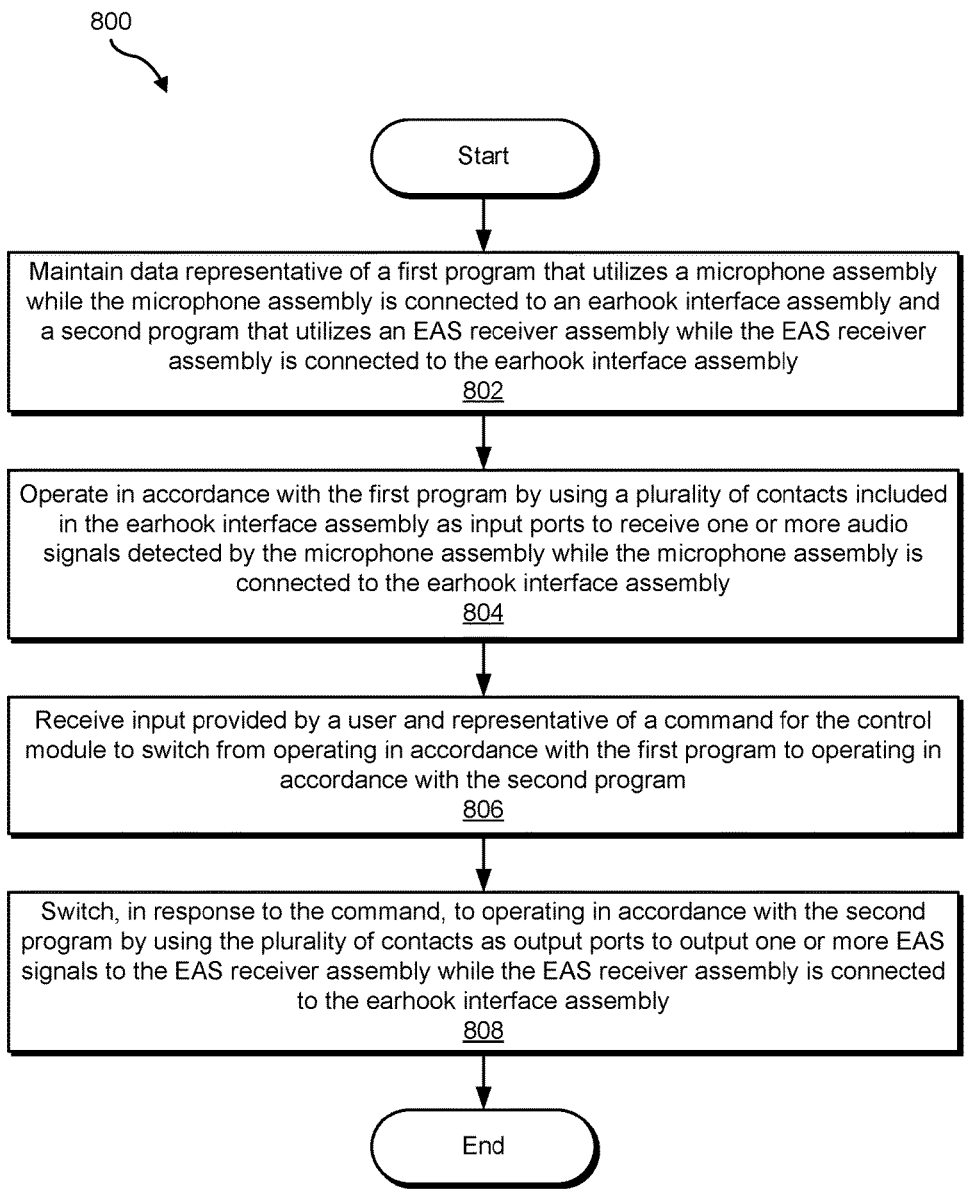
FIG. 8 illustrates an exemplary method of facilitating selective interaction by a control module included within a sound processor apparatus with a microphone assembly and an EAS receiver assembly according to principles described herein.

FIG. 8 illustrates an exemplary method 800 of facilitating selective interaction by a control module included within a sound processor apparatus with a microphone assembly and an EAS receiver assembly. While FIG. 8 illustrates exemplary steps according to one embodiment, other embodiments may omit, add to, reorder, and/or modify any of the steps shown in FIG. 8. One or more of the steps shown in FIG. 8 may be performed by control module 302 and/or any implementation thereof.

In step 802, a control module included in a sound processor apparatus maintains data representative of a first program that utilizes a microphone assembly while the microphone assembly is connected to an earhook interface assembly that comprises a plurality of contacts and that is included in the sound processor apparatus and a second program that utilizes an EAS receiver assembly while the EAS receiver is connected to the earhook interface assembly. Step 802 may be performed in any of the ways described herein.

In step 804, the control module operates in accordance with the first program by using the plurality of contacts as input ports to receive one or more audio signals detected by the microphone assembly while the microphone assembly is connected to the earhook interface assembly. Step 804 may be performed in any of the ways described herein.

In step 806, the control module receives input provided by a user and representative of a command for the control module to switch from operating in accordance with the first program to operating in accordance with the second program. Step 806 may be performed in any of the ways described herein.

In step 808, the control module switches, in response to the command, to operating in accordance with the second program by using the plurality of contacts as output ports to output one or more EAS signals to the EAS receiver assembly while the EAS receiver assembly is connected to the earhook interface assembly. Step 808 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A sound processor apparatus included in an auditory prosthesis system that also includes a cochlear implant configured to be implanted within a patient, the sound processor apparatus comprising:
   an earhook interface assembly that includes a plurality of contacts and that is configured to interchangeably connect, by way of the plurality of contacts, to
      a microphone assembly configured to detect one or more audio signals presented to the patient, and
      an electro-acoustic stimulation ("EAS") receiver assembly configured to apply acoustic stimulation representative of audio content included only in a particular frequency band to the patient, the particular frequency band not including at least one frequency represented by electrical stimulation applied by the cochlear implant; and a control module communicatively coupled to the plurality of contacts and that is configured to use the plurality of contacts as output ports to output one or more EAS signals to the EAS receiver assembly while the EAS receiver assembly is connected to the earhook interface assembly, the one or more EAS signals representative of the audio content included in the particular frequency band that does not include the at least one frequency represented by the electrical stimulation applied by the cochlear implant.

2. The sound processor apparatus of claim 1, wherein the control module is configured to:
detect that the EAS receiver assembly is disconnected from the earhook interface assembly and that the microphone assembly is connected to the earhook interface assembly in place of the EAS receiver assembly; and
switch to using the plurality of contacts as input ports to receive one or more audio signals detected by the microphone assembly while the microphone assembly is connected to the earhook interface assembly.

3. The sound processor apparatus of claim 2, wherein:
the control module comprises analog front end circuitry; and
the control module is configured to use the plurality of contacts as input ports by
connecting a first signal line included within the microphone assembly to the analog front end circuitry, and
connecting a second signal line included within the microphone assembly to ground.

4. The sound processor apparatus of claim 1, wherein:
the control module comprises an EAS driver; and
the control module is configured to use the plurality of contacts as output ports by
connecting a first signal line included within the EAS receiver assembly to a first output of the EAS driver, and
connecting a second signal line included within the EAS receiver assembly to a second output of the EAS driver.

5. The sound processor apparatus of claim 4, wherein the EAS driver is configured to output the one or more EAS signals to the EAS receiver assembly by way of the first and second outputs in accordance with a differential signaling heuristic.

6. The sound processor apparatus of claim 1, wherein the control module comprises a first switch associated with the microphone assembly and a second switch associated with the EAS receiver assembly, wherein the control module is configured to:
close the first switch and open the second switch to operate while the microphone assembly is connected to the earhook interface assembly; and
open the first switch and close the second while the EAS receiver assembly is connected to the earhook interface assembly.

7. The sound processor apparatus of claim 1, wherein the control module is configured to:
detect a connection of the microphone assembly to the earhook interface assembly in place of the EAS receiver assembly; and
automatically switch, in response to the connection of the microphone assembly to the earhook interface assembly, to using the plurality of contacts as input ports to receive one or more audio signals detected by the microphone assembly while the microphone assembly is connected to the earhook interface assembly.

8. The sound processor apparatus of claim 7, wherein the control module is configured to:
detect a connection of the EAS receiver assembly to the earhook interface assembly in place of the microphone assembly; and
automatically switch, in response to the connection of the EAS receiver assembly to the earhook interface assembly, to using the plurality of contacts as output ports to output one or more EAS signals to the EAS receiver assembly while the EAS receiver assembly is connected to the earhook interface assembly.

9. The sound processor apparatus of claim 8, wherein the control module is configured to use another audio source to receive one or more audio signals while the microphone assembly is disconnected from the earhook interface assembly.

10. The sound processor apparatus of claim 1, wherein the microphone assembly comprises a microphone configured to be located within a concha of an ear of a patient associated with the auditory prosthesis system.

11. The sound processor apparatus of claim 1, wherein the plurality of contacts comprises a first contact and a second contact.

12. The sound processor apparatus of claim 1, wherein the earhook interface assembly is further configured to interchangeably connect to an earhook assembly.

13. The sound processor apparatus of claim 12, wherein the control module does not use the plurality of contacts as either input or output ports while the earhook assembly is connected to the earhook interface assembly.

14. A sound processor apparatus included in an auditory prosthesis system that also includes a cochlear implant configured to be implanted within a patient, the sound processor apparatus comprising:
an earhook interface assembly that includes a plurality of contacts and that is configured to interchangeably connect, by way of the plurality of contacts, to
a microphone assembly configured to detect one or more audio signals presented to the patient, and
an electro-acoustic stimulation ("EAS") receiver assembly configured to apply acoustic stimulation representative of audio content included only in a particular frequency band to the patient, the particular frequency band not including at least one frequency represented by electrical stimulation applied by the cochlear implant; and
a control module communicatively coupled to the plurality of contacts and that:
maintains data representative of a first program that utilizes the microphone assembly and a second program that utilizes the EAS receiver assembly; and
operates in accordance with the second program by using the plurality of contacts as output ports to output one or more EAS signals to the EAS receiver assembly while the EAS receiver assembly is connected to the earhook interface assembly, the one or more EAS signals representative of the audio content included in the particular frequency band that does not include the at least one frequency represented by the electrical stimulation applied by the cochlear implant.

15. The sound processor apparatus of claim 14, wherein the control module:
receives input provided by a user and representative of a command for the control module to switch from operating in accordance with the second program to operating in accordance with the first program; and switches, in response to the command, to operating in accordance with the first program by using the plurality of contacts as input ports to receive one or more audio signals detected by the microphone assembly while the microphone assembly is connected to the earhook interface assembly.

16. The sound processor apparatus of claim 15, wherein the plurality of contacts comprises a first contact and a second contact.

17. The sound processor apparatus of claim 16, wherein the control module comprises analog front end circuitry, and, while operating in accordance with the first program, the control module uses the first and second contacts as input ports by:

connecting a first signal line included within the microphone assembly to the analog front end circuitry; and connecting a second signal line included within the microphone assembly to ground.

18. The sound processor apparatus of claim 16, wherein the control module comprises an EAS driver, and, while operating in accordance with the first program, the control module uses the first and second contacts as output ports by:

connecting a first signal line included within the EAS receiver assembly to a first output of the EAS driver; and connecting a second signal line included within the EAS receiver assembly to a second output of the EAS driver.

19. A method comprising:

maintaining, by a control module included in a sound processor apparatus that is a part of an auditory prosthesis system that also includes a cochlear implant configured to be implanted within a patient, data representative of a first program that utilizes a microphone assembly while the microphone assembly is connected to an earhook interface assembly that comprises a plurality of contacts and that is included in the sound processor apparatus, and a second program that utilizes an electro-acoustic stimulation ("EAS") receiver assembly configured to apply acoustic stimulation representative of audio content included only in a particular frequency band to the patient while the EAS receiver assembly is connected to the earhook interface assembly, the particular frequency band not including at least one frequency represented by electrical stimulation applied by the cochlear implant; and operating, by the control module, in accordance with the second program by using the plurality of contacts as output ports to output one or more EAS signals to the EAS receiver assembly while the EAS receiver assembly is connected to the earhook interface assembly.

20. The method of claim 19, further comprising:

receiving, by the control module, input provided by a user and representative of a command for the control module to switch from operating in accordance with the second program to operating in accordance with the first program; and switching, by the control module in response to the command, to operating in accordance with the first program by using the plurality of contacts as input ports to receive one or more audio signals detected by the microphone assembly while the microphone assembly is connected to the earhook interface assembly.

* * * * *